United States Patent [19]

Umezawa et al.

[11] Patent Number: 4,876,244
[45] Date of Patent: Oct. 24, 1989

[54] MEDICAL COMPOSITION FOR INJECTION CONTAINING A SPERGUALIN AS ACTIVE INGREDIENT AND PROCESS FOR PREPARING THE SAME

[75] Inventors: Hamao Umezawa; Shintaro Suzuki; Taka'aki Ohkuma; Fumihiro Sato, all of Tokyo; Teruya Nakamura, Kusatsu, all of Japan

[73] Assignee: Zaidan Hojin Biseibutsu Kagaku, Tokyo, Japan

[21] Appl. No.: 84,167

[22] Filed: Aug. 11, 1987

Related U.S. Application Data

[62] Division of Ser. No. 817,266, Jan. 9, 1986, Pat. No. 4,710,517.

[30] Foreign Application Priority Data

Jan. 14, 1985 [JP] Japan .................................. 60-3351

[51] Int. Cl.$^4$ ............................................. A61K 37/02
[52] U.S. Cl. ..................................... 514/19; 514/970; 514/616
[58] Field of Search ...................... 514/616.2, 21, 644, 514/19, 970

[56] References Cited

U.S. PATENT DOCUMENTS

| | | | |
|---|---|---|---|
| 4,416,899 | 11/1983 | Umezawa et al. | 424/320 |
| 4,430,346 | 2/1984 | Umezawa et al. | 424/311 |
| 4,518,532 | 5/1985 | Umezawa et al. | 564/157 |
| 4,525,299 | 6/1985 | Umezawa et al. | 424/320 |
| 4,529,549 | 7/1985 | Umezawa et al. | 548/342 |
| 4,556,735 | 12/1985 | Umezawa et al. | 564/137 |
| 4,710,517 | 12/1987 | Umezawa | 514/616 |

OTHER PUBLICATIONS

*Remington Pharmaceutical Science*, 16th ed., Osol editor, Mack Publishing Co., pp. 252 and 1483, 1980.
*The Merck Index*, 9th ed., Martha Windholz editor, Merck and Co., Inc., Rahway, N.J., 1976, entry Nos. 2904, 2909, 4217, 8212 and 5575.

*Primary Examiner*—Delbert R. Phillips
*Assistant Examiner*—F. T. Moezie
*Attorney, Agent, or Firm*—Banner, Birch, McKie & Beckett

[57] ABSTRACT

The present invention relates to a stable medical composition for injection containing (1) a Spergualin of the formula:

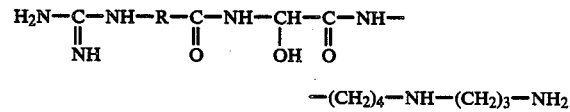

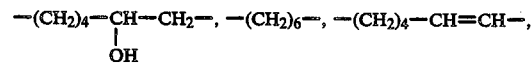

[wherein R is

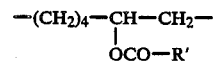

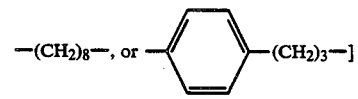

(wherein R' is a lower alkyl group having 1 to 4 carbon atoms),

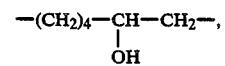

or a salt thereof and (2) at least one stabilizer selected from the group consisting of mannitol, maltose, dextran, lactose, cyclodextrin, gelatin, chondroitin sulfate, and human serum albumin; when R is $$-(CH_2)_4-CH-CH_2-,$$
$$\phantom{-(CH_2)_4-}OH$$

mannitol is excepted.

A spergualin is useful as cancer control agents and immunomodulators.

14 Claims, No Drawings

MEDICAL COMPOSITION FOR INJECTION CONTAINING A SPERGUALIN AS ACTIVE INGREDIENT AND PROCESS FOR PREPARING THE SAME

BACKGROUND OF THE INVENTION

1. Field of the Invention

This invention relates to a medical composition for injection containing a Spergualin as active ingredient and a process for preparing the same.

2. Description of the Prior Art

Spergualins (I) are useful drugs having cancer control and immunomodulating activities and they have the following structure (see U.S. Pat. Nos. 4,430,346, 4,525,299, and 4,529,549):

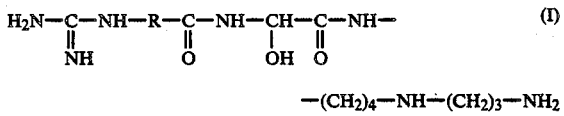

$-(CH_2)_4-NH-(CH_2)_3-NH_2$ wherein R is

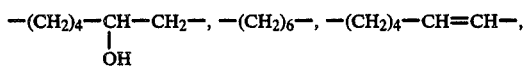

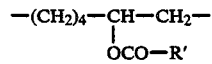

(wherein R' is a lower alkyl group having 1 to 4 carbon atoms,.

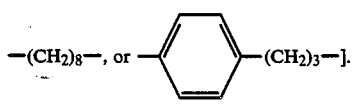

Spergualins are labile in aqueous solutions and lose their activity as a result of hydrolysis into the following compounds (II) and (III):

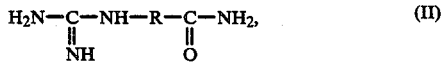

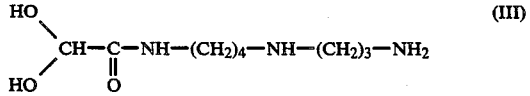

Such substances which are labile in aqueous solutions are conventionally formulated as injections by one of the following two methods: the active ingredient is either dried to a powder form or otherwise solidified by freeze-drying and is converted to an aqueous solution just before use; or the active ingredient is dissolved in non-aqueous solvents such as alcohols and vegetable oils. In the latter method, ethanol, glycerin, propylene glycol and polyethylene glycol 400 are predominantly used as water-miscible non-aqueous solvents, but because of high local toxicity these solvents must be diluted with water before injection. Vegetable oils and other water-immiscible non-aqueous solvents cannot be administered intravenously unless they are emulsified with the aid of surfactants.

Therefore, in order to prepare Spergualin injections that can be administered intraveneously or locally by, for example, intramuscular injection, the first of the two methods shown above is preferred, that is, Spergualin is dried to a powder form or otherwise solidified by freeze-drying and is subsequently converted to an aqueous solution. However, Spergualin is highly hygroscopic and will deliquesce even at a relative humidity of 14% (25° C.). In addition, it is very difficult to obtain Spergualin as crystal.

Therefore, Spergualin alone cannot be easily dried into a powder form or freeze-dried into a solid form having good appearance. Furthermore, a highly hygroscopic drug such as Spergualin defies complete elimination of adsorbed water or may often absorb water during the process of preparing the desired formulation or during transportation or subsequent storage. In the presence of adsorbed water, many excipients will either accelerate the decomposition of the active ingredient or decompose by themselves. For whichever reason, the formulation becomes labile and cannot be used as a stable injection that can be placed on the market.

SUMMARY OF THE INVENTION

The present inventors made various studies in order to prepare stable freeze-dried Spergualin injections suitable for placement on the market. As a result, the inventors have found that this object can be attained by using as stabilizers one or more members selected from the group consisting of mannitol, maltose, dextran, lactose, cyclodextrin, chondroitin sulfate, gelatin and human serum albumin. The present invention has been completed on the basis of this finding.

A single stabilizer selected from this group may be used, but two or more stabilizers may also be used in suitable combinations.

DETAILED DESCRIPTION OF THE INVENTION

The Spergualins used in the present invention have the formula (I) shown above, wherein R is

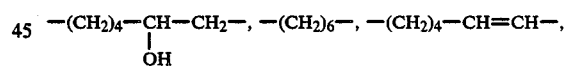

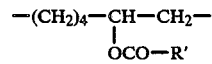

(wherein R' is a lower alkyl group having 1 to 4 carbon atoms),

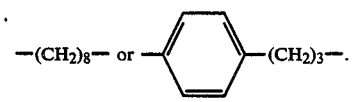

Typical examples of the Spergualins meeting this requirements are listed below:

(1) 1-Amino-19-guanidino-11,15-dihydroxy-4,9,12-triazanonadecan-10,13-dione (Spergualin);

(2) 1-Amino-19-guanidino-11-hydroxy-4,9,12-triazanonadecan-10,13-dione (15-deoxyspergualin);

(3) 1-Amino-19-guanidino-11-hydroxy-4,9,12-triazanonadecan-14-en-10,13-dione (15-deoxy-14-enspergualin);

(4) 15-Acetyl-1-amino-19-guanidino-11-hydroxy-4,9,12-triazanonadecan-10,13-dione (15-o-acetylspergualin);
(5) 15-Propionyl-1-amino-19-guanidino-11-hydroxy-4,9,12-triazanonadecan-10,13-dione (15-o-propionylspergualin);
(6) 1-Amino-21-guanidino-11-hydroxy-4,9,12-triazaheneicosan-10,13-dione; and
(7) 1-Amino-16-p-guanidinophenyl-11-hydroxy-4,9,12-triazahexadecan-10,13-dione.

These Spergualins may be racemic forms or optically active forms containing an optically active carbon atom. The Spergualins may be in the form of any medically acceptable salts and they include mineral acids such as hydrochloric acid, sulfuric acid and phosphoric acid; organic sulfonic acids such as toluenesulfonic acid, benzenesulfonic acid and methanesulfonic acid; carboxylic acid such as acetic acid, dibasic acids such as succinic acid and maleic acid; and tribasic acids such as citric acid.

Stabilizers that can be used in the present invention include mannitol, maltose, dextran, lactose, cyclodextrin, chondroitin sulfate, gelatin and human serum albumin (when R is

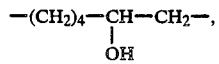

mannitol is excepted). Maltose, lactose, chondroitin sulfate, gelatin and human serum albumin are preferred.

These stabilizers may be added in any amounts that are not smaller than 0.2 part by weight per a part of the Spergualins, and they are usually used in amounts ranging from about 0.5 to 100 parts, preferably 1 to 50 parts, more preferably 1 to 20 parts by weight.

A ratio of spergualins to total amount of the medical composition is 5 to 80 W/W %, preferably 15 to 60 W/W %, more preferably 25 to 50 W/W %. A ratio of stabilizers to total amount of the medical composition is 20 to 95 W/W %, preferably 40 to 85 W/W %, more preferably 50 to 75 W/W %.

For the purpose of pH adjustment, the Spergualin formulation in accordance with the present invention may contain acids, alkalis or suitable amounts of buffers. Spergualins will remain stable in aqueous solutions at pHs not higher than about 5, but they are adjusted to pHs between 2 and 8, preferably between 3 and 7 when they are formulated in a solid form by freeze-drying.

The medical composition of the present invention may be prepared by the following procedures. Spergualins and stabilizers are dissolved in water of which temperature is 0° to 40° C., preferably 0 to 30° C., and after optical adjustment to a suitable pH, the solution is sterilized by passage through a membrane filter and is subsequently dried by, for example, freeze-drying. The water is preferably distilled water for injection, and is used in an amount that is not smaller than 10 parts by weight per part of the Spergualins, and it is preferably used in an amount ranging from 20 to 200 parts by weight.

Stability test was conducted with the samples prepared in Examples 1 to 10 (see below), a control that was freeze-dried in the absence of any stabilizer, and other four control samples that were prepared as in the Examples except that glucose, fructose, glycine and alanine were respectively added in two parts as stabilizers for one part of 15-deoxyspergualin. The test results are shown in Table 1. In the stability test, the samples were held in a thermostated chamber at 50° C. for 10 days, and thereafter, the Spergualin content of each sample was measured by HPLC and its appearance was visually checked.

TABLE 1

Stability of Freeze-dried Spergualin Preparations (10-day storage at 50° C.)

| Sample | | Initial Appearance | Appearance | Spergualin content (%) |
|---|---|---|---|---|
| Samples of the invention | Example 1 | WS | WS | 97.4 |
| | 2 | WS | WS | 98.7 |
| | 3 | WS | WS | 92.5 |
| | 4 | WS | WS | 88.1 |
| | 5 | WS | WS | 95.1 |
| | 6 | WS | WS | 100.1 |
| | 7 | WS | PYS | 99.4 |
| | 8 | WS | WS | 90.3 |
| | 9 | WS | WS | 96.5 |
| | 10 | WS | WS | 99.7 |
| Control sample | No stabilizer | Colorless glass | Pale yellow glass | 70.7 |
| | Glucose | WS | Pale yellow syrup | 46.4 |
| | Fructose | WS | Brown syrup | 32.5 |
| | Glycine | WS | PYS | 44.8 |
| | Alanine | WS | PYS | 49.7 |

Notes:
WS, white, freeze-dried solid; PYS, pale yellow, freeze-dried solid; "Spergualin content" is indicated in terms of relative value with the initial value taken as 100.

As the above data show, the samples in accordance with the present invention retained Spergualin level of not less than 88% after the 10-day storage at 50° C. whereas even the stablest control sample exhibited a Spergualin level of only 70.7%. Most of the samples in accordance with the invention retained their initial appearance. Therefore, it can be concluded that the formulations of the invention have a very high time-dependent stability.

The present invention is hereunder described in greater detail by reference to Examples, wherein all parts are by weight.

EXAMPLE 1

A drug solution having the following composition was prepared.

| 15-Deoxyspergualin | 1 part |
|---|---|
| Maltose | 2 parts |
| 1N HCl (adjusted to pH 4.0) | q.s. |
| Distilled water for injection | q.s. to 50 parts |

The solution thus prepared was sterilized by passage through a membrane filter and distributed among glass containers, which were freeze-dried and sealed to make injections.

EXAMPLE 2

A drug solution having the following composition was prepared.

| 15-Deoxyspergualin | 1 part |
|---|---|
| Lactose | 2 parts |
| 1N HCl (adjusted to pH 4.0) | q.s. |
| Distilled water for injection | q.s. to |

-continued

| | 50 parts |

The solution thus prepared was sterilized by passage through a membrane filter and distributed among glass containers, which were freeze-dried and sealed to make injections.

EXAMPLE 3

A drug solution having the following composition was prepared.

| 15-Deoxyspergualin | 1 part |
| Dextran 40 | 2 parts |
| 1N HCl (adjusted to pH 4.0) | q.s. |
| Distilled water for injection | q.s. to 50 parts |

The solution thus prepared was sterilized by passage through a membrane filter and distributed among glass containers, which were freeze-dried and sealed to make injections.

EXAMPLE 4

A drug solution having the following composition was prepared.

| 15-Deoxyspergualin | 1 part |
| Mannitol | 2 parts |
| 1N HCl (adjusted to pH 4.0) | q.s. |
| Distilled water for injection | q.s. to 50 parts |

The solution thus prepared was sterilized by passage through a membrane filter and distributed among glass containers, which were freeze-dried and sealed to make injections.

EXAMPLE 5

A drug solution having the following composition was prepared.

| 15-Deoxyspergualin | 1 part |
| β-cyclodextrin | 1 part |
| 1N HCl (adjusted to pH 4.0) | q.s. |
| Distilled water for injection | q.s. to 50 parts |

The solution thus prepared was sterilized by passage through a membrane filter and distributed among glass containers, which were freeze-dried and sealed to make injections.

EXAMPLE 6

A drug solution having the following composition was prepared.

| 15-Deoxyspergualin | 1 part |
| Chondroitin sulfate | 2 parts |
| 1N HCl (adjusted to pH 4.0) | q.s. |
| Distilled water for injection | q.s. to 50 parts |

The so prepared solution was sterilized by passage through a membrane filter and distributed among glass containers, which were freeze-dried and sealed to make injections.

EXAMPLES 7

A drug solution having the following composition was prepared.

| 15-Deoxyspergualin | 1 part |
| Gelatin | 2 parts |
| 1N HCl (adjusted to pH 4.0) | q.s. |
| Distilled water for injection | q.s. to 50 parts |

The so prepared solution was sterilized by passage through a membrane filter and distributed among glass containers, which were freeze-dried and sealed to make injections.

EXAMPLE 8

An injection was prepared as in Example 1 except that 15-deoxyspergualin was replaced by Spergualin.

EXAMPLE 9

An injection was prepared as in Example 2 except that 15-deoxyspergualin was replaced by Spergualin.

EXAMPLE 10

A drug solution having the following formulation was prepared.

| Spergualin | 1 part |
| Human serum albumin | 1 part |
| 1N HCl (pH adjusted to 4.0) | q.s. |
| Distilled water for injection | q.s. to 50 parts |

The so prepared solution was sterilized by passage through a membrane filter and distributed among glass containers, which were freeze-dried and sealed to make injections.

EXAMPLE 11

An injection was prepared as in Example 1 except that 15-deoxyspergualin was replaced by 15-deoxy-14-enspergualin and that the amount of maltose was increased to 10 parts.

EXAMPLE 12

An injection was prepared as in Example 2 except that 15-deoxyspergualin was replaced by 15-o-propionyl-spergualin and that the amount of lactose was increased to 5 parts.

EXAMPLE 13

An injection was prepared as in Example 3 except that 15-deoxyspergualin was replaced by 1-amino-21-guanidino-11-hydroxy-4,9,12-triazaheneicosan-10,13-dione.

EXAMPLE 14

An injection was prepared as in Example 7 except that 15-deoxyspergualin was replaced by 1-amino-16-p-guanidinophenyl-11-hydroxy-4,9,12-triazahexadecan-10,13-dione and that the amount of gelatin was decreased to 1 part.

EXAMPLE 15

An injection was prepared as in Example 6 except that 15-deoxyspergualin was replaced by 15-o-acetyl-spergualin.

What is claimed is:

1. A freeze dried composition for injection containing (1) a compound of the formula:

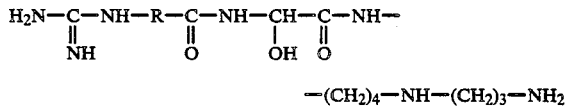

or a salt thereof, wherein R is

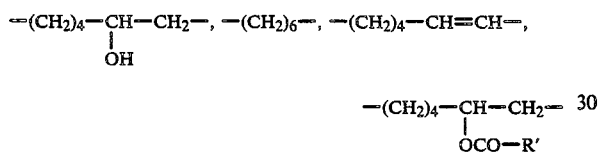

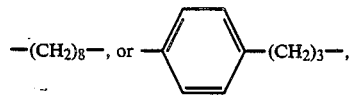

(wherein R' is a lower alkyl group having 1 to 4 carbon atoms),

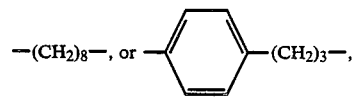

and (2) at least one stabilizer selected from the group consisting of dextran, cyclodextrin, and chondroitin sulfate.

2. A freeze dried composition according to claim 1, wherein the compound is
1-amino-19-guanidino-11,15-dihydroxy-4,9,12-triazanonadecan-10,13-dione (Spergualin);
1-amino-19-guanidino-11-hydroxy-4,9,12-triazanonadecan-10,13-dione (15-deoxyspergualin);
1-amino-19-guanidino-11-hydroxy-4,9,12-triazanonadecan-14-en-10,13-dione (15-deoxy-14-enspergualin);
15-acetyl-1-amino-19-guanidino-11-hydroxy-4,9,12-triazanonadecan-10,13-dione (15-o-acetylspergualin);
15-propionyl-1-amino-19-guanidino-11-hydroxy-4,9,12-triazanonadecan-10,13-dione (15-o-propionylspergualin);
1-amino-21-guanidino-11-hydroxy-4,9,12-triazaheneicosan-10,13-dione; or
1-amino-16-p-guanidinophenyl-11-hydroxy-4,9,12-triazahexadecan-10,13-dione.

3. A freeze dried composition according to claim 1, wherein the stabilizer is chondroitin sulfate.

4. A freeze dried composition according to claim 1, wherein an amount of the stabilizer is 0.5 to 100 parts by weight per a part of the compound.

5. A freeze dried composition according to claim 1, wherein a ratio of the compound to total amount of the composition is 5 to 80 W/W %, and a ratio of the stabilizers to total amount of the composition is 20 to 95 W/W %.

6. A freeze dried composition for injection containing
(1) a compound of the formula:

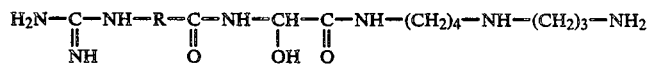

or a salt thereof, wherein R is

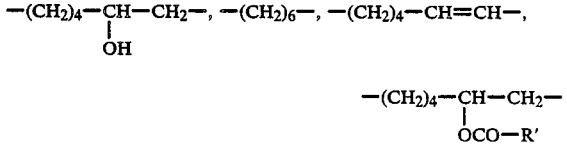

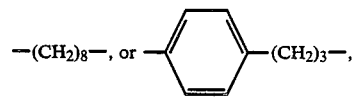

(wherein R' is a lower alkyl group having 1 to 4 carbon atoms),

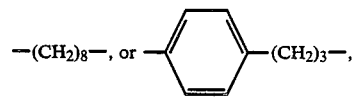

and (2) at least one stabilizer selected from the group consisting of gelatin and human serum albumin.

7. A freeze dried composition according to claim 6, wherein the compound is
1-amino-19-guanidino-11,15-dihydroxy-4,9,12-triazanonadecan-10,13-dione (Spergualin);
1-amino-19-guanidino-11-hydroxy-4,9,12-triazanonadecan-10,13-dione (15-deoxyspergualin);
1-amino-19-guanidino-11-hydroxy-4,9,12-triazanonadecan-14-en-10,13-dione (15-deoxy-14-enspergualin);
15-acetyl-1-amino-19-guanidino-11-hydroxy-4,9,12-triazanonadecan-10,13-dione (15-o-acetylspergualin);
15-propionyl-1-amino-19-guanidino-11-hydroxy-4,9,12-triazanonadecan-10,13-dione (15-o-propionylspergualin);
1-amino-21-guanidino-11-hydroxy-4,9,12-triazaheneicosan-10,13-dione; or
1-amino-16-p-guanidinophenyl-11-hydroxy-4,9,12-triazahexadecan-10,13-dione.

8. A freeze dried composition according to claim 6, wherein an amount of the stabilizer is 0.5 to 100 parts by weight per a part of the compound.

9. A freeze dried composition according to claim 6, wherein a ratio of the compound to total amount of the composition is 5 to 80 W/W %, and a ratio of the stabilizer to the total amount of the composition is 20 to 95 W/W %.

10. A freeze dried composition for injection containing
(1) a compound of the formula:

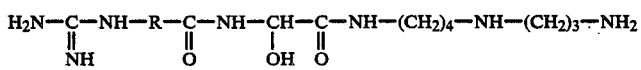

or a salt thereof, wherein R is

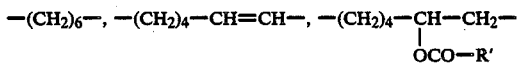

(wherein R' is a lower alkyl group having 1 to 4 carbon atoms),

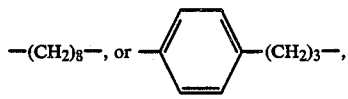

and
(2) mannitol as a stabilizer.

11. A freeze dried composition according to claim 10, wherein the compound is
1-amino-19-guanidino-11-hydroxy-4,9,12-triazanonadecan-10,13-dione (15-deoxyspergualin);
1-amino-19-guanidino-11-hydroxy-4,9,12-triazanonadecan-14-en-10,13-dione (15-deoxy-14-enspergualin);
15-acetyl-1-amino-19-guanidino-11-hydroxy-4,9,12-triazanonadecan-10,13-dione (15-o-acetylspergualin);
15-propionyl-1-amino-19-guanidino-11-hydroxy-4,9,12-triazanonadecan-10,13-dione (15-o-propionylspergualin);
1-amino-21-guanidino-11-hydroxy-4,9,12-triazaheneiconsan-10,13-dione; or
1-amino-16-p-guanidinophenyl-11-hydroxy-4,9,12-triazahexadecan-10,13,dione.

12. A freeze dried composition according to claim 10, wherein an amount of the stabilizer is 0.5 to 100 parts by weight per a part of the compound.

13. A freeze dried composition according to claim 10, wherein a ratio of the compound to total amount of the composition is 5 to 80 W/W %, and a rate of the stabilizer to total amount of the composition is 20 to 95 W/W %.

14. A freeze dried composition for injection according to claim 10 containing 1-amino-19-guanidino-11-hydroxy-4,9,12-triazanonadecan-10,13-dione (15-deoxyspergualin) and mannitol.

* * * * *